(12) United States Patent
Nuzum et al.

(10) Patent No.: US 12,070,361 B2
(45) Date of Patent: Aug. 27, 2024

(54) PROTECTIVE SHIELD FOR SURGICAL MICROSCOPE

(71) Applicant: Micah Nuzum, Wooster, OH (US)

(72) Inventors: Micah Nuzum, Wooster, OH (US); John P. Cichello, Wooster, OH (US)

(*) Notice: Subject to any disclaimer, the term of this patent is extended or adjusted under 35 U.S.C. 154(b) by 677 days.

(21) Appl. No.: 17/314,823

(22) Filed: May 7, 2021

(65) Prior Publication Data

US 2021/0346113 A1 Nov. 11, 2021

Related U.S. Application Data

(60) Provisional application No. 63/134,510, filed on Jan. 6, 2021, provisional application No. 63/030,978, filed on May 28, 2020, provisional application No. 63/021,848, filed on May 8, 2020.

(51) Int. Cl.
  *A61B 90/00* (2016.01)
  *A61B 46/10* (2016.01)
  *A61B 50/00* (2016.01)
  *A61B 90/20* (2016.01)
  *G02B 21/00* (2006.01)

(52) U.S. Cl.
  CPC ............. *A61B 90/05* (2016.02); *A61B 46/10* (2016.02); *A61B 50/00* (2016.02); *A61B 90/20* (2016.02); *G02B 21/0012* (2013.01)

(58) Field of Classification Search
  CPC ................................. A61B 90/20; A61B 46/10
  See application file for complete search history.

(56) References Cited

U.S. PATENT DOCUMENTS

| | | | |
|---|---|---|---|
| 3,926,185 A | * 12/1975 | Krzewinski | A61B 46/00 128/854 |
| 4,274,716 A | 6/1981 | Gammon | |
| 4,618,222 A | 10/1986 | Eisenberg | |
| 4,730,880 A | 3/1988 | Schmidt et al. | |
| 4,848,322 A | * 7/1989 | Dash | A61B 90/05 128/857 |
| 4,936,318 A | 6/1990 | Schoolman | |
| 4,976,254 A | 12/1990 | Dash et al. | |
| 5,024,212 A | * 6/1991 | Bonnet | A61B 90/05 600/105 |
| 5,305,765 A | * 4/1994 | Potts | A61F 13/00 128/853 |

(Continued)

FOREIGN PATENT DOCUMENTS

CN 203965718 U * 11/2014
CN 210005781 U * 1/2020

(Continued)

*Primary Examiner* — Christopher Stanford
(74) *Attorney, Agent, or Firm* — COATS & BENNETT, PLLC

(57) ABSTRACT

A protective shield for a surgical microscope provides a barrier between a doctor and a patient that is undergoing a surgical procedure. The protective shield is designed to removably mount to the surgical microscope so that the shield can be replaced or removed for sterilization. The protective shield provides protection to the doctor who is placing his/her eyes directly against the binoculars of the microscope without impeding the view through the binoculars. The shield blocks splatter and other bodily fluids coming from in front of or below the lens or operating area.

22 Claims, 19 Drawing Sheets

(56) References Cited

U.S. PATENT DOCUMENTS

| | | | |
|---|---|---|---|
| 5,341,513 A * | 8/1994 | Klein | A61F 9/027 |
| | | | 128/857 |
| 5,360,018 A | 11/1994 | Chen | |
| 5,522,403 A * | 6/1996 | Bark | A61B 90/40 |
| | | | 128/853 |
| 5,782,750 A | 7/1998 | Gluskin | |
| 5,865,182 A | 2/1999 | Chen | |
| 5,947,894 A * | 9/1999 | Chapman | A61B 90/05 |
| | | | 128/857 |
| 6,116,741 A | 9/2000 | Paschal | |
| 6,695,773 B1 * | 2/2004 | Dahlinger | A61B 90/05 |
| | | | 128/857 |
| 10,175,467 B2 | 1/2019 | Mazel et al. | |
| 10,231,495 B2 | 3/2019 | Nabai | |
| 10,466,176 B2 | 11/2019 | Rochford et al. | |
| 10,517,550 B2 | 12/2019 | Gordon | |
| 10,603,217 B2 | 3/2020 | Spier | |
| 2019/0381265 A1 * | 12/2019 | Banuelos | A61M 16/0084 |

FOREIGN PATENT DOCUMENTS

| | | | |
|---|---|---|---|
| CN | 210697977 U * | 6/2020 | |
| JP | 2002118157 A * | 4/2002 | |
| JP | 3571112 B2 * | 9/2004 | |

* cited by examiner

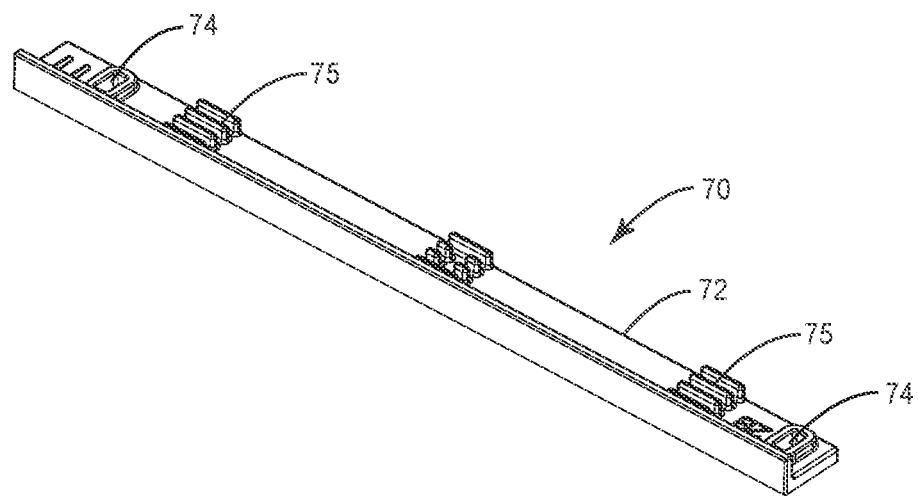
*FIG. 13A*
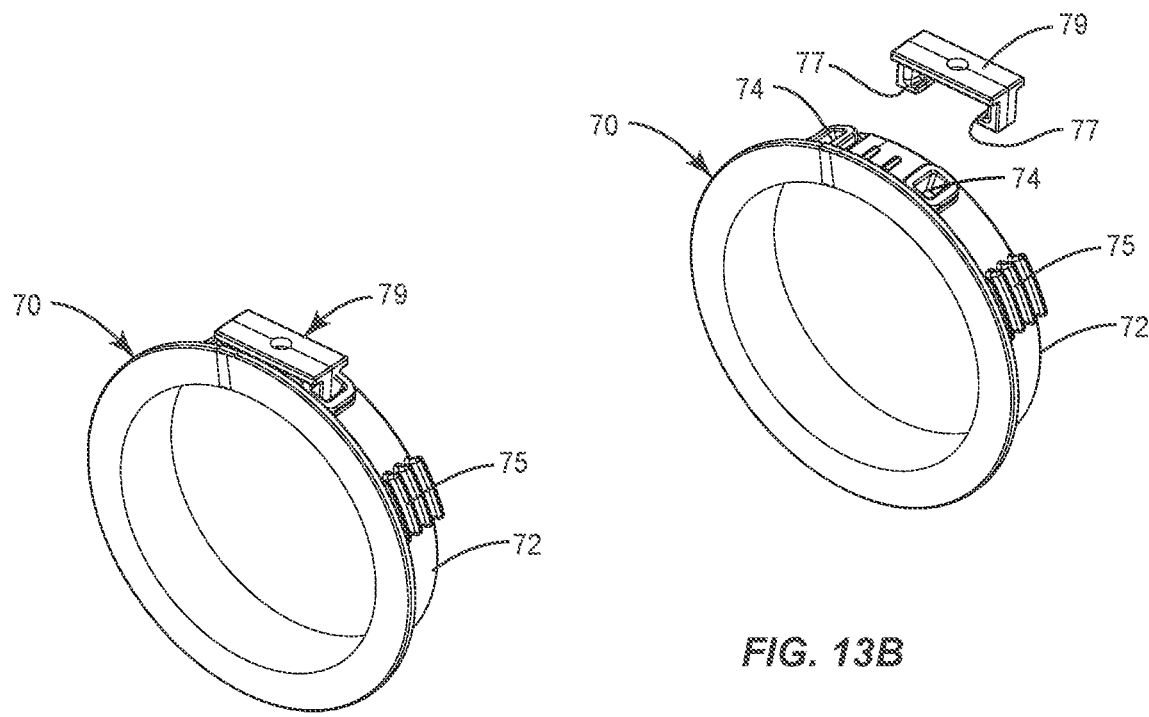
*FIG. 13B*
*FIG. 13C*

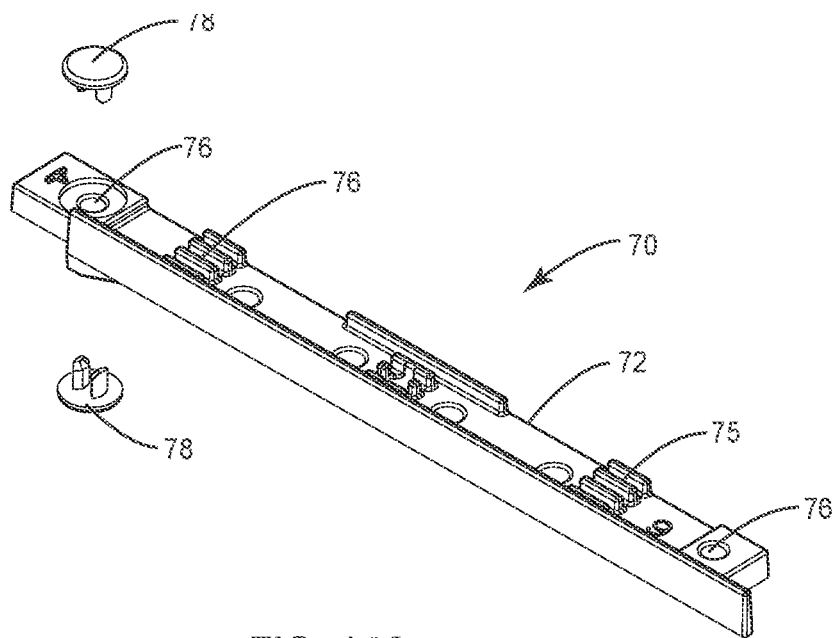
FIG. 14A
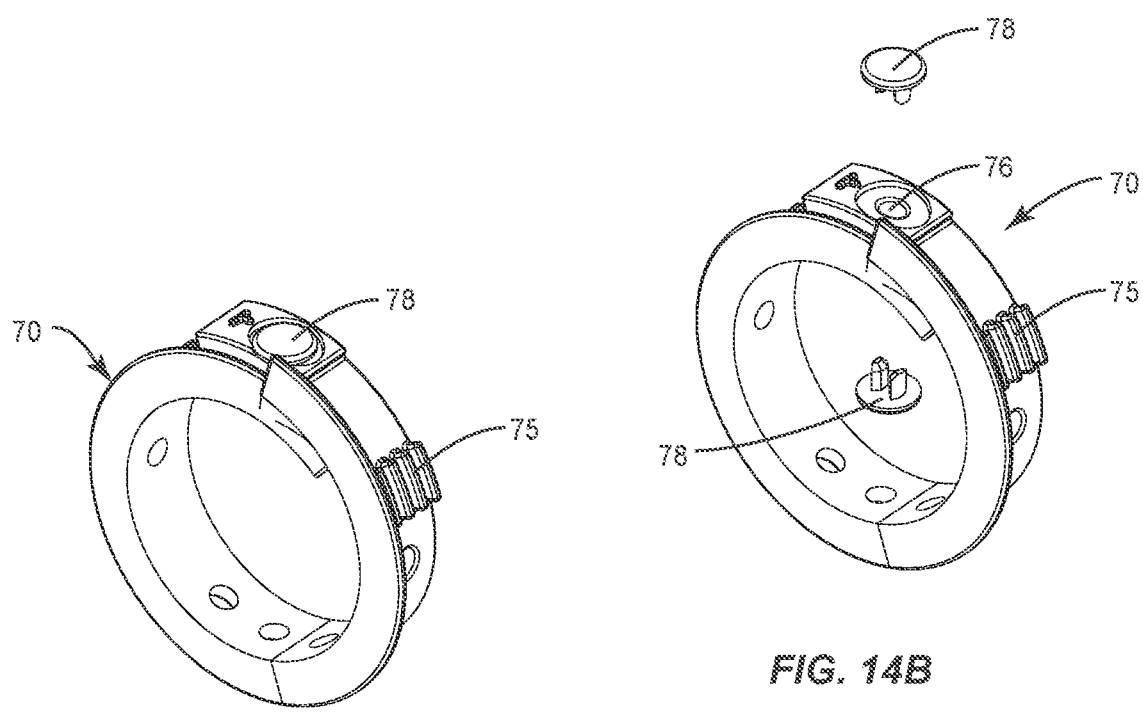
FIG. 14B
FIG. 14C

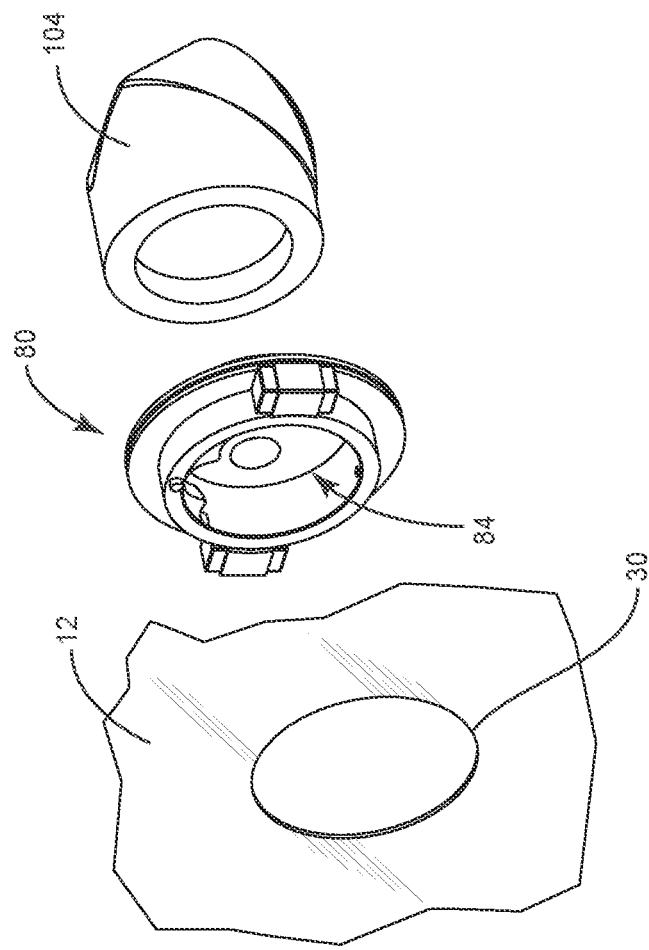
FIG. 16
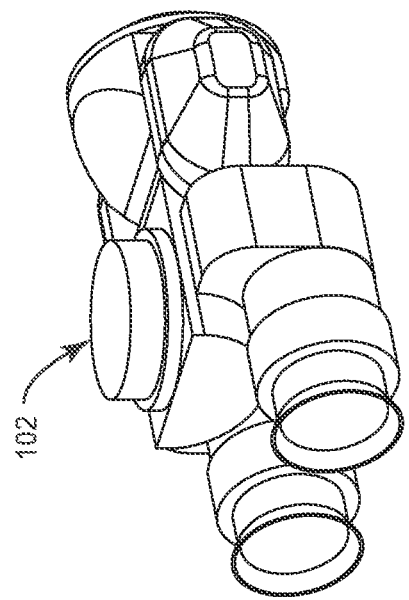

PROTECTIVE SHIELD FOR SURGICAL MICROSCOPE

RELATED APPLICATIONS

The present application claims benefit of U.S. Provisional Application 63/021,848, which was filed May 8, 2020, U.S. Provisional Application 63/030,978, which was filed May 28, 2020, and U.S. Provisional Application 63/134,510, which was filed Jan. 6, 2021, the disclosures of each of which are incorporated herein by reference in their entirety.

TECHNICAL FIELD

The present disclosure relates generally to surgical microscopes; and, more particularly to protective shields for surgical microscopes to protect both the patient and surgeon.

BACKGROUND

In the practice of endodontics, the transmission of infections during an endodontic procedure has always been a significant concern for both patients and dental health care providers. The recent spread of severe acute respiratory syndrome coronavirus 2 (SARS-CoV-2) has only heightened these concerns. It is known that SARS-CoV-2 is present in the saliva of affected patients. Thus, endodontists are at high risk of becoming infected if they do not take appropriate precautions.

Endodontic procedures are commonly performed with the aid of a surgical microscope. The surgical microscope provides improved visualization through magnification and illumination of the operating site and enables the endodontists to operate with more precision and with improved outcomes. During endodontic procedures, the endodontists will be exposed to splash-back and splatter from the operating site. Even with the use of surgical gowns and masks, the endodontists is not fully protected. One area of concern is eye protection. An endodontist may forgo the use of goggles or other eye protection because it can interfere with the use of the surgical microscope. Also, the upper check, neck and ears of the endodontists may be exposed. Therefore, protective equipment is needed to provide greater protection and prevent the spread of infectious diseases during surgical procedures involving the use of surgical microscopes.

SUMMARY

The present disclosure relates to a protective shield for a surgical microscope that provides a barrier between a doctor and a patient that is undergoing a surgical procedure. The protective shield is designed to removably mount to the surgical microscope so that the shield can be replaced or removed for sterilization. The protective shield provides protection to the doctor who is placing his/her eyes directly against the binoculars of the microscope without impeding the view through the binoculars. The shield blocks splatter and other bodily fluids coming from in front of or below the lens or operating area.

According to one aspect, the protective shield comprises a flexible shield made of a transparent sheet material with a central opening that fits around the surgical microscope and a frame bent to form an arc curving concavely towards the user when the protective shield is mounted to the surgical microscope. The frame is configured to removably attach to an upper edge of the flexible shield to hold the flexible shield in a curved configuration forming a concave arc around the user.

According to another aspect, the protective shield comprises a transparent shield with a central opening that fits around the surgical microscope. The transparent shield has a curved configuration forming a concave arc around the user when mounted to the surgical microscope. A slot extends from the central opening to one side of the transparent shield.

BRIEF DESCRIPTION OF THE DRAWINGS

FIGS. 13A-13C illustrate a seal for the protective shield.

FIGS. 14A-14C illustrate another seal for the protective shield.

FIG. 16 is an exploded perspective view of an adapter for mounting the protective shield to the surgical microscope.

DETAILED DESCRIPTION

Figure 1:
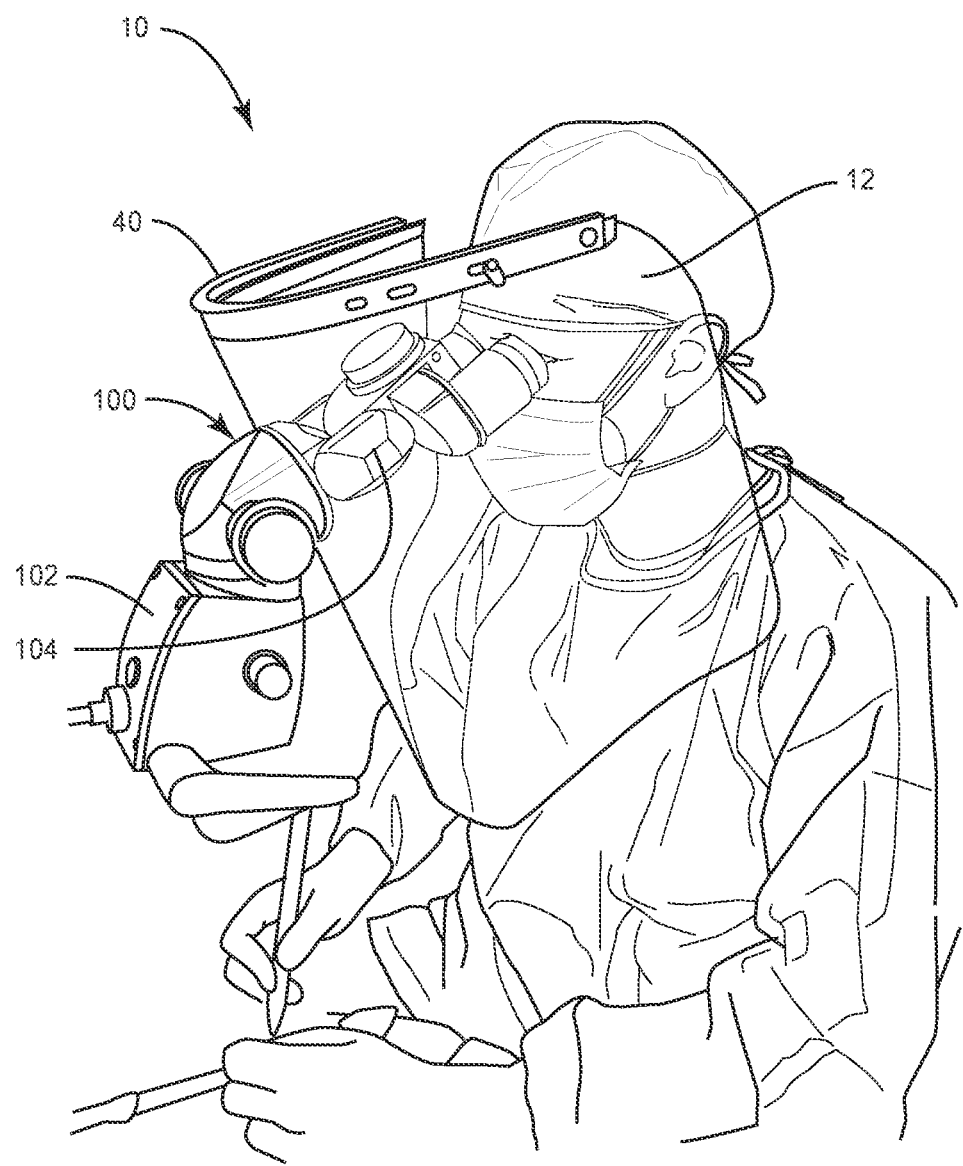
FIG. 1 is a perspective view of the protective shield in use.
Figure 2:
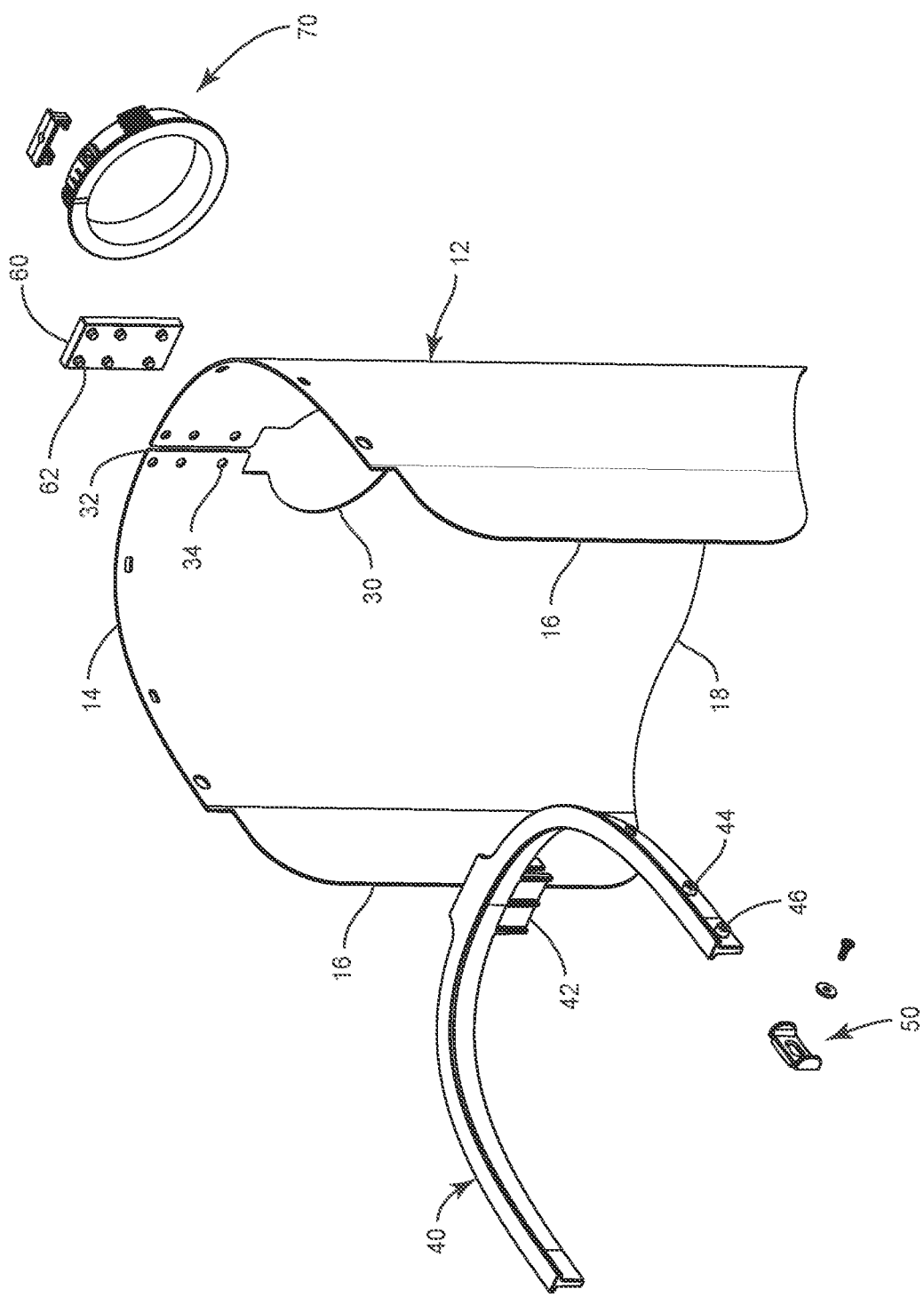
FIG. 2 is an exploded perspective view of a protective shield according to a first embodiment.
Figure 3:
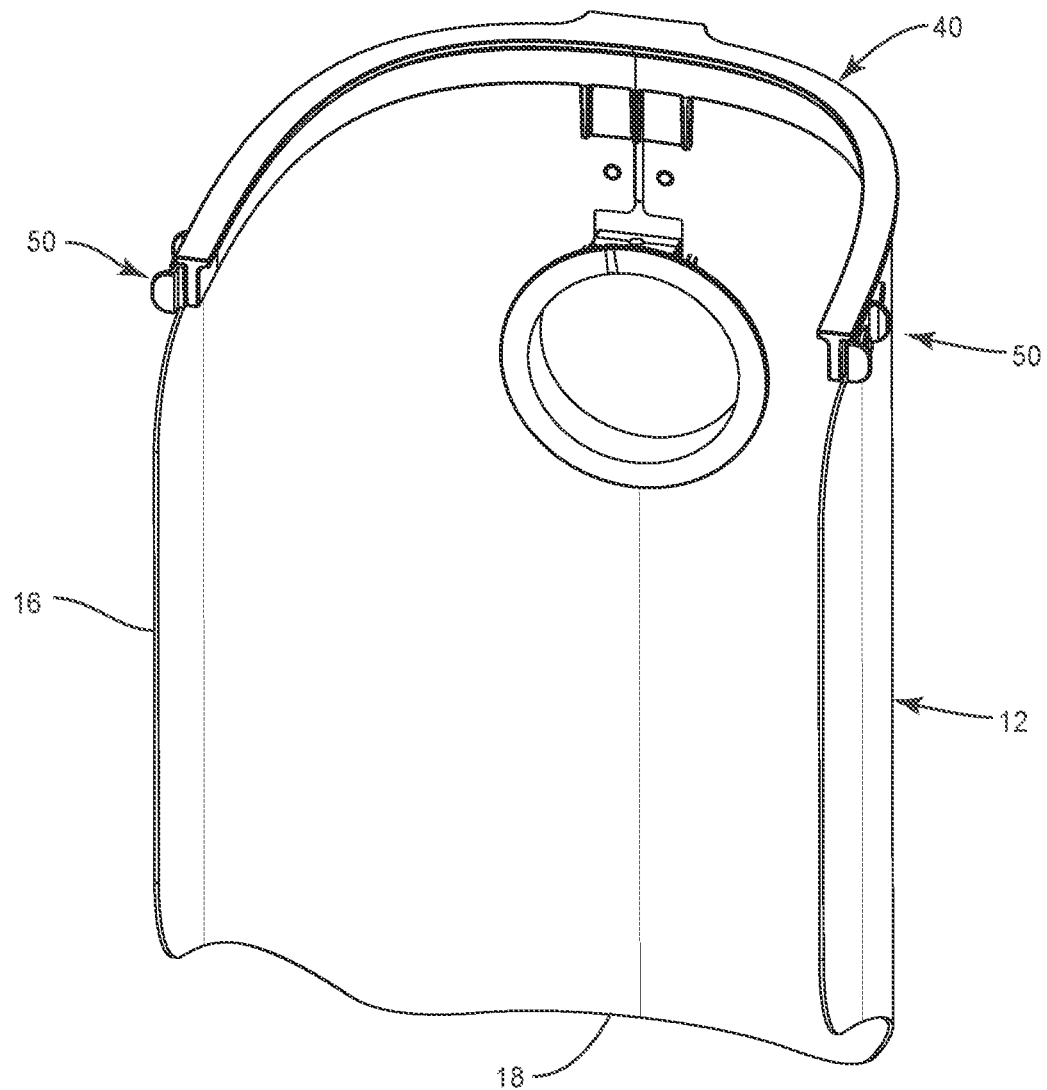
FIG. 3 is a perspective view of the protective shield according to the first embodiment from the rear.
Figure 4:
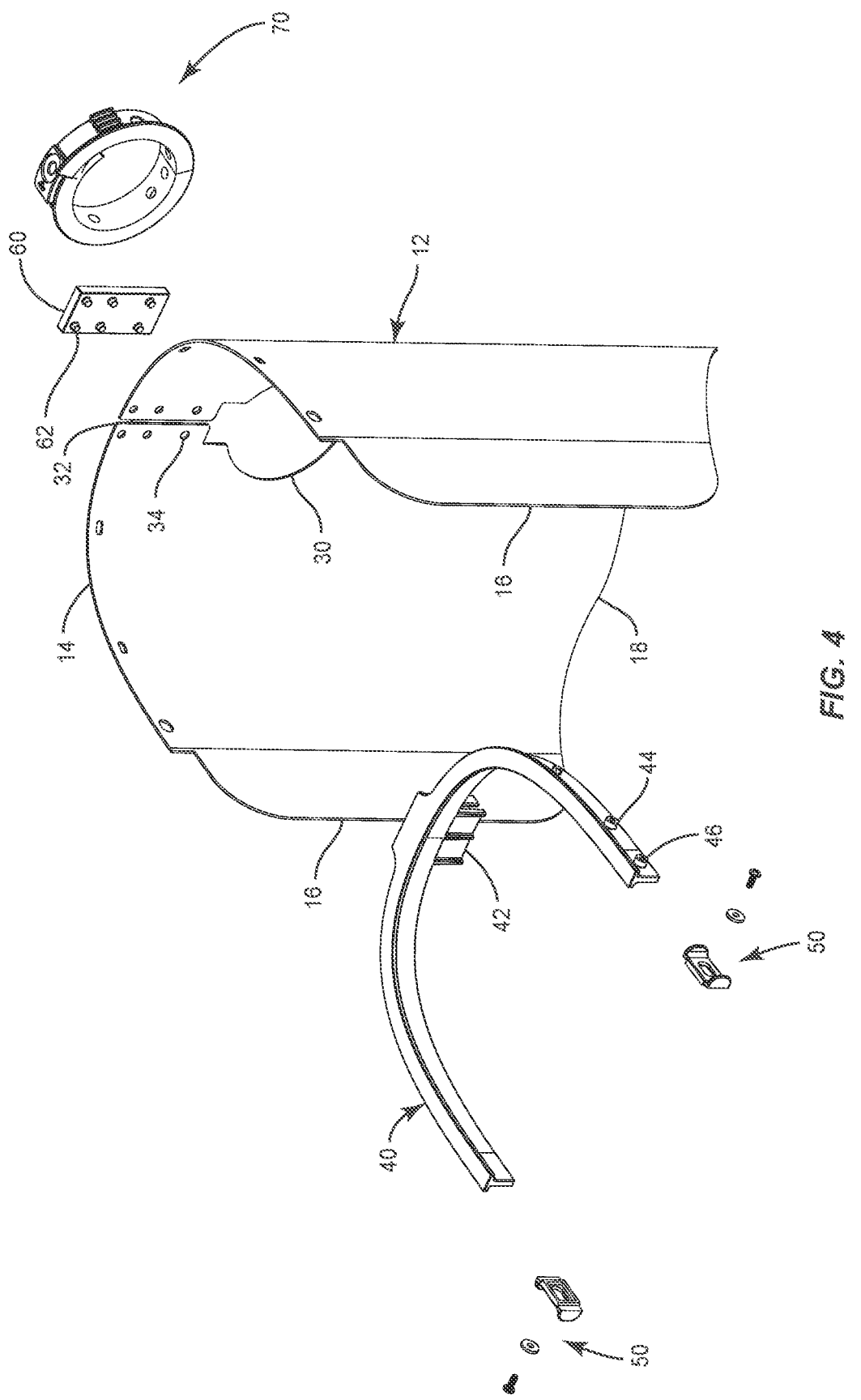
FIG. 4 is an exploded perspective view of a protective shield according to a second embodiment.
Figure 5:
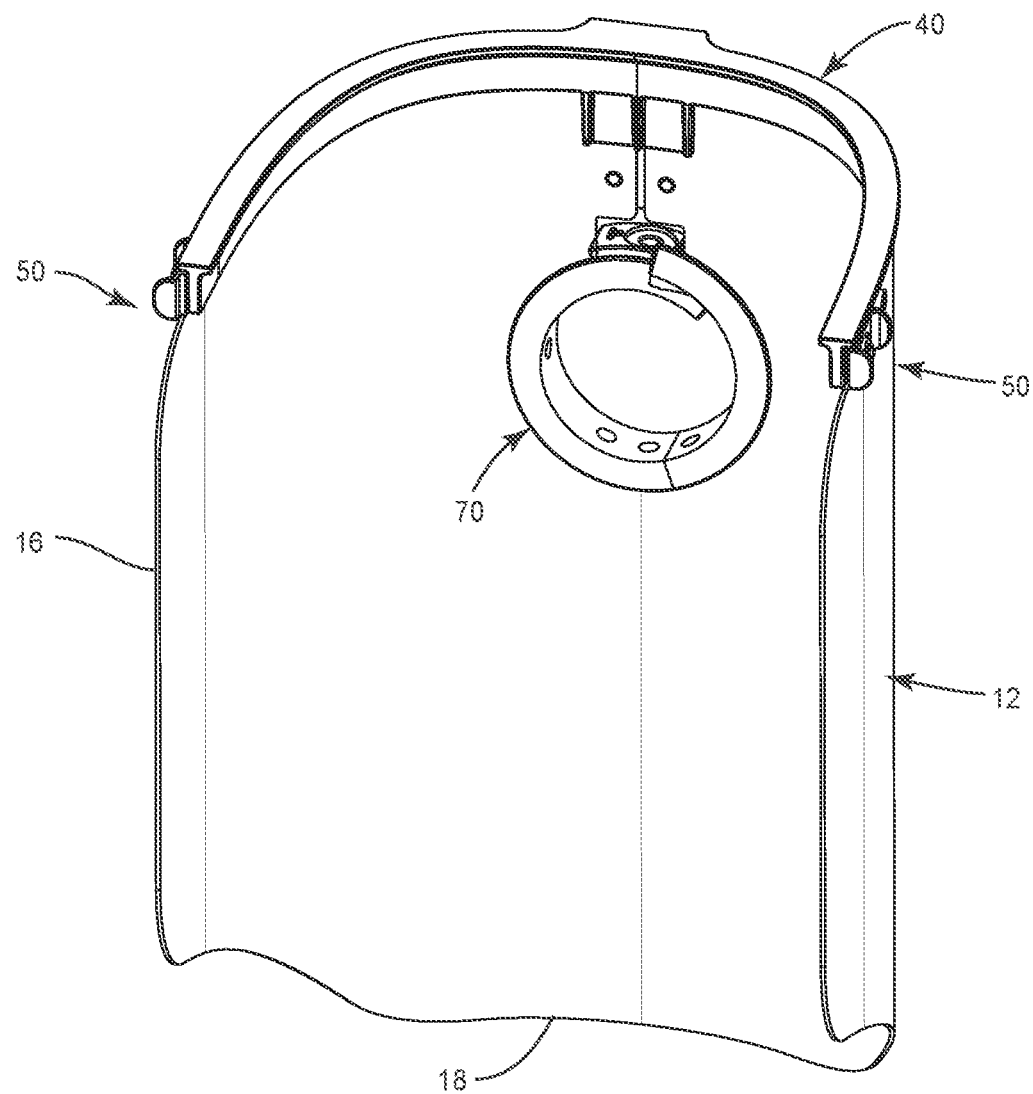
FIG. 5 is a perspective view of the protective shield according to the second embodiment from the rear.

Referring now to the drawings, and particularly to FIG. 1, an exemplary embodiment of a protective shield 10 in the context of a surgical microscope 100 used in the practice of dentistry and/or endodontics. It will be appreciated from the following description, however, that the protective shield is not limited to the practice of dentistry or endodontics, but rather is more generally appliable to any surgical or medical procedure involving the use of a surgical microscope or other optical instrument to visualize the operating side or area under inspection.

The protective shield 10 is designed to removably mount to the surgical microscope 100 so that the protective shield 10 can be replaced or removed for sterilization. The protective shield 10 provides a barrier between a doctor and a patient that is undergoing a surgical procedure. The protective shield 10 provides protection to the doctor who is placing his/her eyes directly against the binoculars of the surgical microscope 100 without impeding the view through the binoculars. The protective shield 10 blocks splatter and other bodily fluids coming from the operating area in front of and/or below the lens.

FIGS. 2-7 illustrates three embodiments of the protective shield 10. For convenience, similar reference numerals are used in drawings and descriptions to indicate similar elements or components.

The protective shield 10 comprises two main components: a transparent shield 12 and a frame 40. The transparent shield 12 is designed to fit around the surgical microscope 100 and the frame 40 attaches to an upper edge of the transparent shield 12. The purpose of the frame 40 is to hold the transparent shield 12 in a predetermined shape. The frame 40 is bent to form an arc curving concavely around the user and holds the flexible shield in a curve configuration when the transparent shield 12 is secured to the frame 40.

Figure 8:
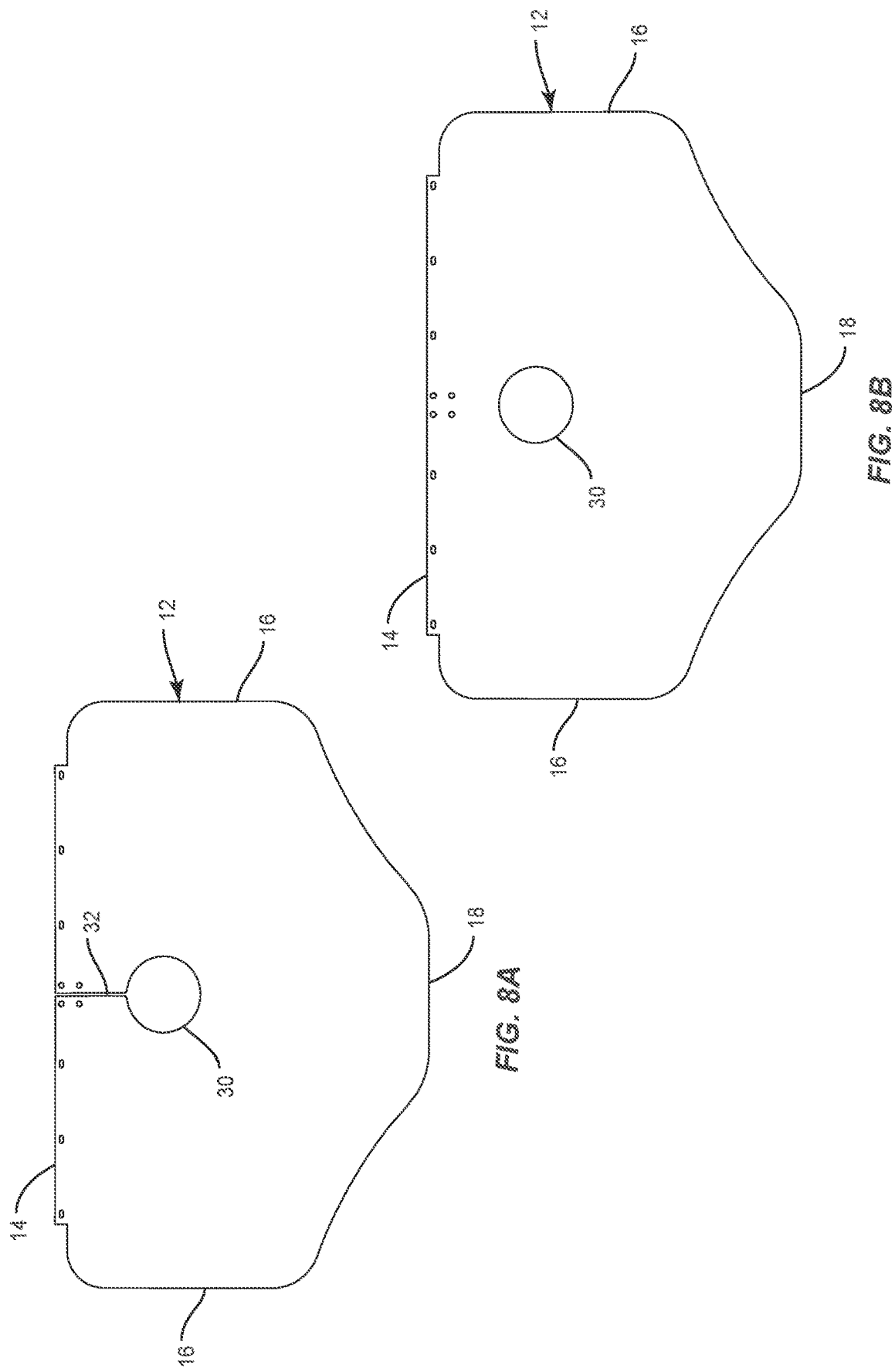
FIG. 8A illustrates a transparent shield with a slot.
FIG. 8B illustrates a transparent shield without a slot.

In one embodiment, the transparent shield 12 made is made from a flexible sheet material, such as polyurethane, polycarbonate or flexible glass. For example, the sheet material may comprise a ⅟₁₆-inch polycarbonate sheet. FIG. 8 illustrates the profile of the transparent shield 12 according to an exemplary embodiment, although the shape can vary depending on various factors such as the desired amount of protection and physical constraints imposed by the geometry of the surgical microscope 100.

The transparent shield 12 has a generally rectangular shape with the lower right and left corners truncated to provide improved access to the surgical site(s) by reducing obstruction of the operator's arms. The transparent shield 12 includes a straight top edge 14 that attaches to the frame 40, vertical side edges 16, and a bottom edge 18. The top edge 14 steps down as it nears each side edge 16 to form a shoulder 20. The bottom edge 18 is generally flat in the center and angles upward towards each side edge 16 to provide clearance for the operator's arms. A series of openings or slots 22 are formed along the top edge 14 to receive respective pegs or studs 44 on the frame 40. As will be hereinafter described, the pegs or studs 44 register with respective openings or slots 22 to locate and align the transparent shield 12 with respect to the frame 40.

Figure 6:
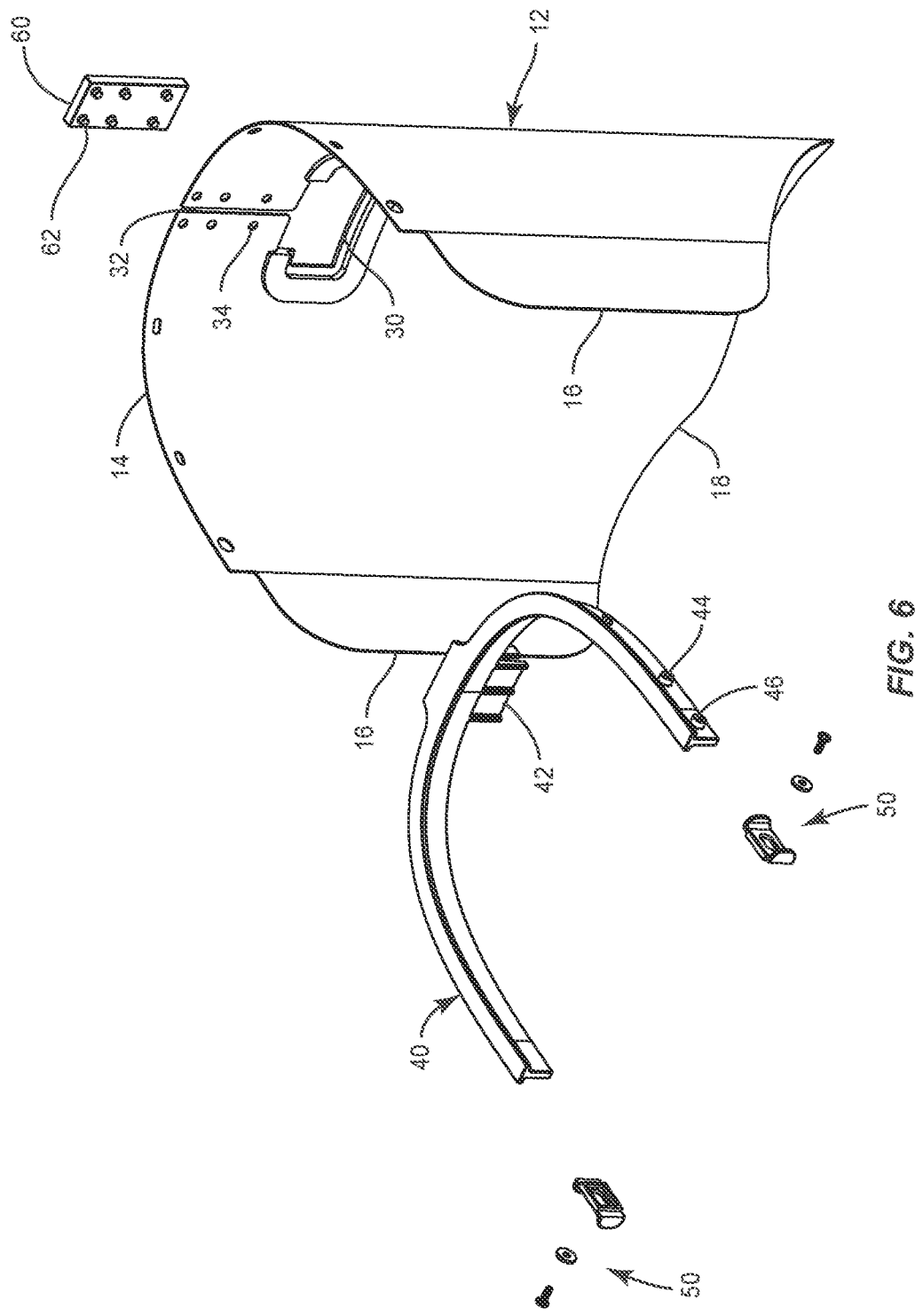
FIG. 6 is an exploded perspective view of a protective shield according to a third embodiment.
Figure 7:
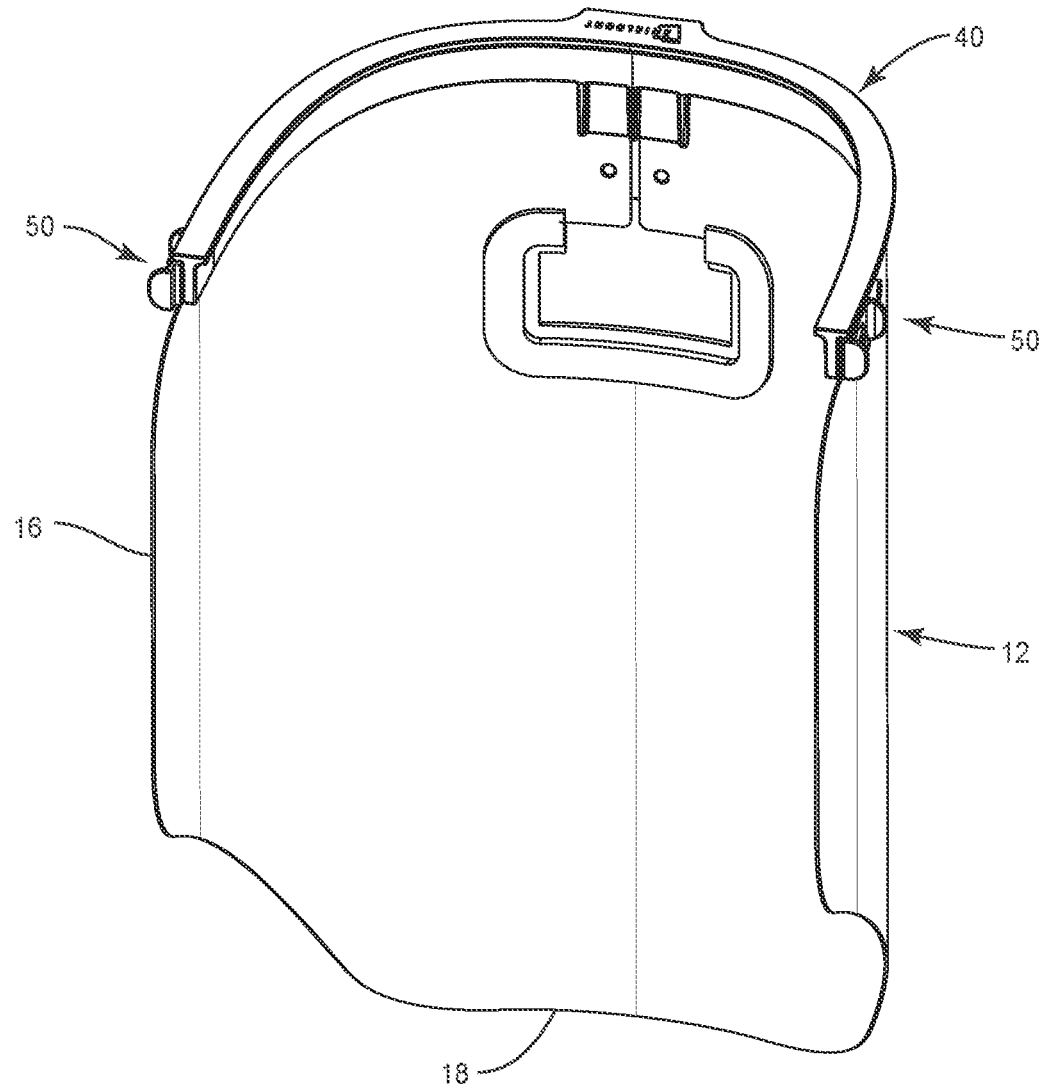
FIG. 7 is a perspective view of the protective shield according to the third embodiment from the rear.

The transparent shield 12 further incudes a central opening 30 through which a portion of the surgical microscope 100 extends. The shape and size of the central opening 30 can vary depending on the particular model of the microscope 100 for which the protective shield 10 is designed. Current major manufacturers of microscopes are Zeiss, Global Surgical, and Leica. Generally, the central opening 30 is sized and shaped to fit around a portion of the surgical microscope 100. In the embodiments shown in FIGS. 2-5, the central opening is circular while the central opening in the embodiments shown in FIGS. 6 and 7 is generally rectangular.

In preferred embodiments, a slot 32 extends from the central opening 30 to the top edge 14 of the shield to facilitate mounting of the transparent shield 12 to the microscope 100 without dismantling the microscope 100. Alternatively, the slot 32 could extend from the central opening 30 to a side edge 16 or bottom edge 18 of the transparent shield 12. In the absence of the slot 32, the binoculars will likely need to be dismounted from the adapter or main body of the microscope 100 to install the protective shield 10.

The frame 40 comprises a generally T-shaped member including a generally horizontal cap and a generally vertical leg extending perpendicularly downward from the cap. The frame 40 is made from any substantially rigid material, such as metal or plastic. The frame 40 is bent into an arc of the desired curvature and includes a mounting plate 42 at its center. The frame 40 has sufficient rigidity to retain its shape when the transparent shield 12 is attached. The top edge 14 of the transparent shield 12 attaches to the frame 40 and the transparent shield 112 is bent to conform to the arc of the frame 40. The transparent shield 12 can then be secured to the frame 40 by any suitable fasteners, such as nut and bolt fasteners, screws, rotating clips, etc. The frame 40 holds the transparent shield 12 in a suitable arc around the doctor or surgeon when the transparent shield 12 is secured to the frame 40.

In a preferred embodiment, the frame 40 extends along the upper edge only of the transparent shield 12 and does not extend align the sides or bottom edge of the transparent shield. Keeping the sides and bottom "frameless" prevents blocking or interference with the surgeon's field of view. In some embodiments, the frame 40 may extend partially down the sides from the top of the frame while the bottom edge is frameless.

In one embodiment, the frame 40 includes a series of pegs or studs 44 that insert into corresponding openings 22 along the top edge of the transparent shield 12. in some embodiments, the pegs or studs 44 are configured to provide a snap fit or frictional fit to hold the transparent shield 12.

Figure 9:
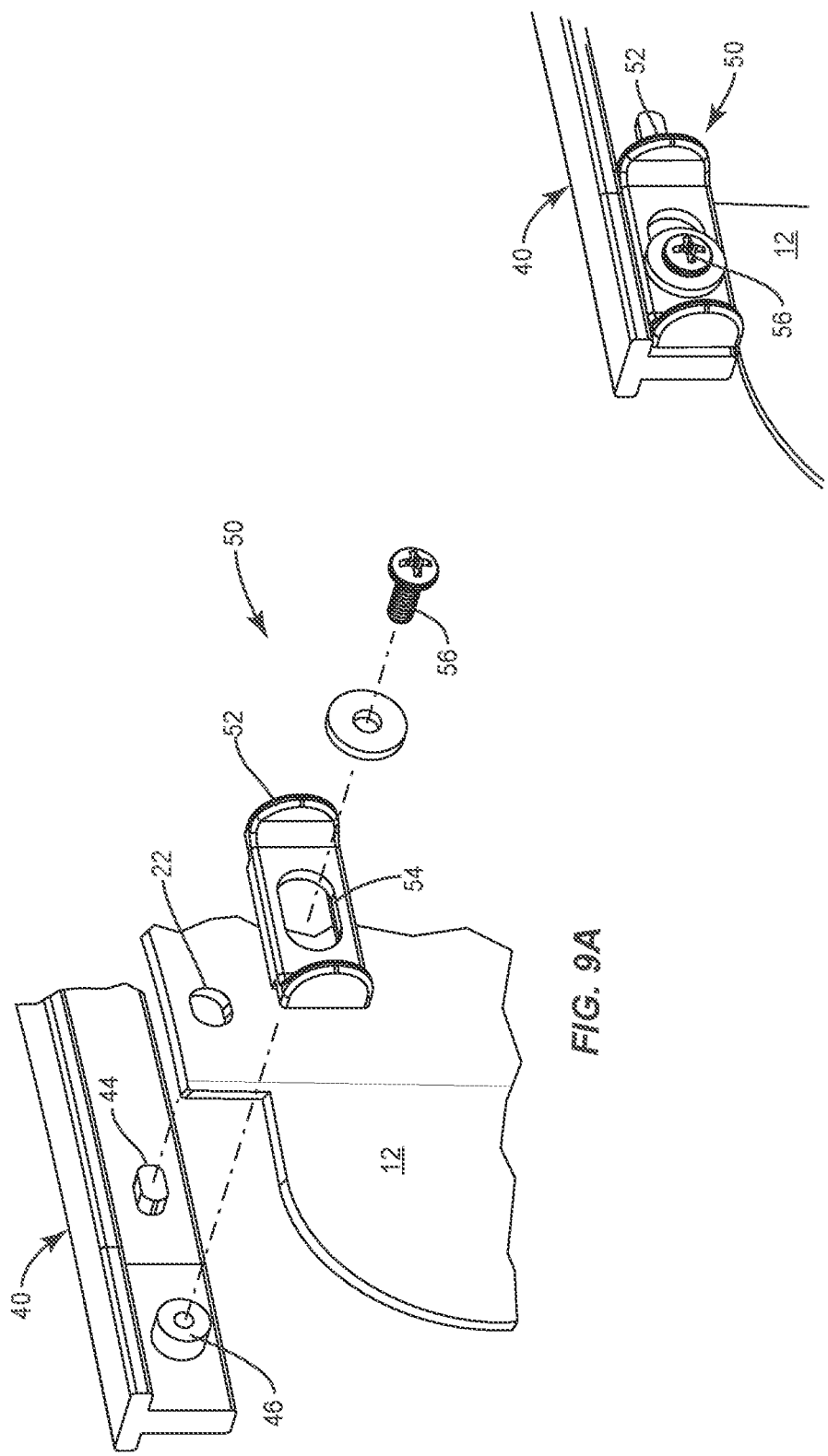
FIG. 9A is a perspective view of a latch for securing the protective shield to the frame.
FIG. 9B is an exploded perspective view of a latch for securing the protective shield to the frame.
Figure 10:
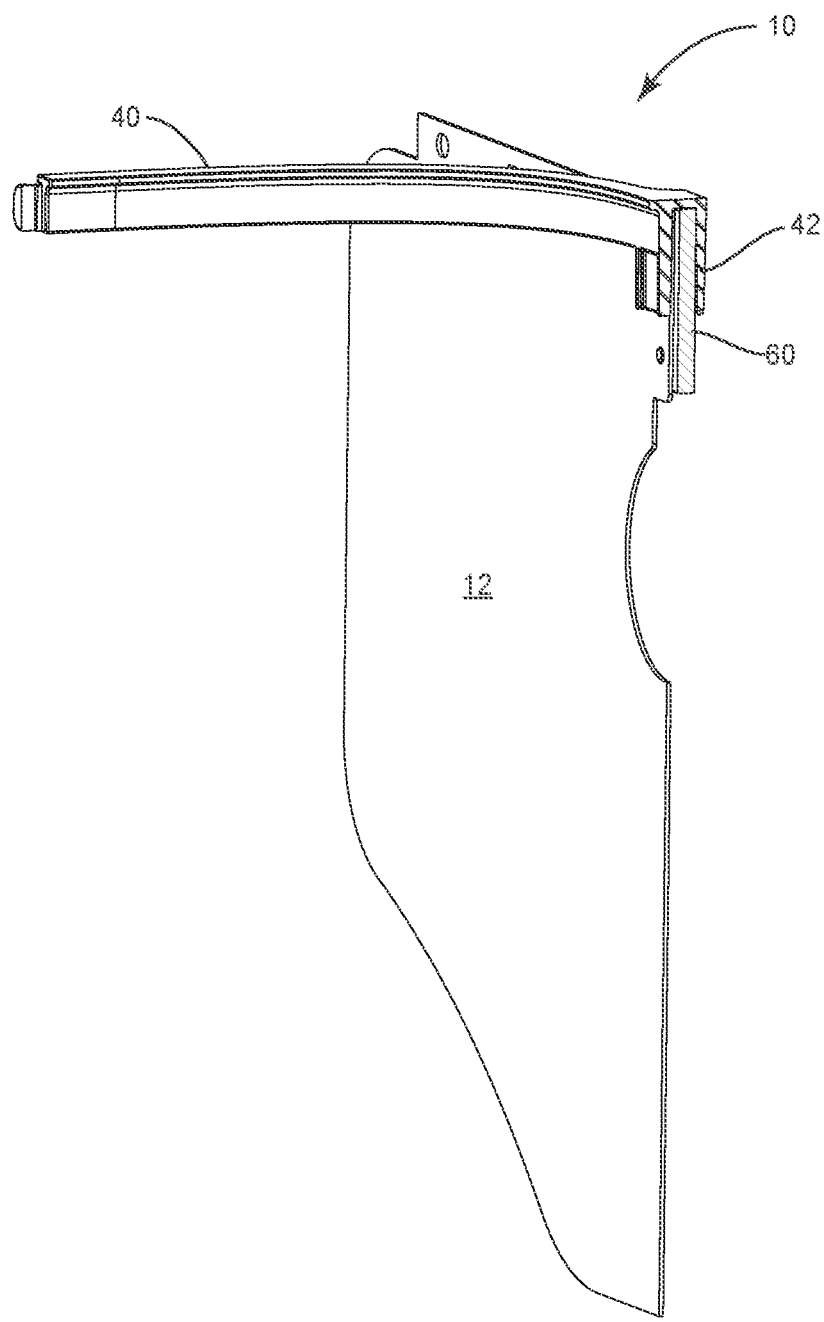
FIG. 10 is a section perspective of the protective shield.

In some embodiments, a locking member 50, shown in FIGS. 9 and 10, is mounted adjacent each end of the frame 40 for more permanently securing the transparent shield to the frame 40. The locking member 50 comprises a slide 52 having a slot 54 formed therein. The slide 52 mounts over a post 46 on the end of the frame 40 and is secured by a locking screw 56 that screws into a threaded opening in the post 46. Once the transparent shield 12 is engaged with the studs 44 on the frame 40, the slide 52 can slide over the edge of the transparent shield 12 to prevent the transparent shield 12 from separating from the frame 40 due to the natural resiliency of the transparent shield 12 and its tendency to return to a flattened condition. After sliding the slide 52 over the transparent shield 12, the locking screw 56 is tightened to lock the slide 52 in place.

Figure 11:
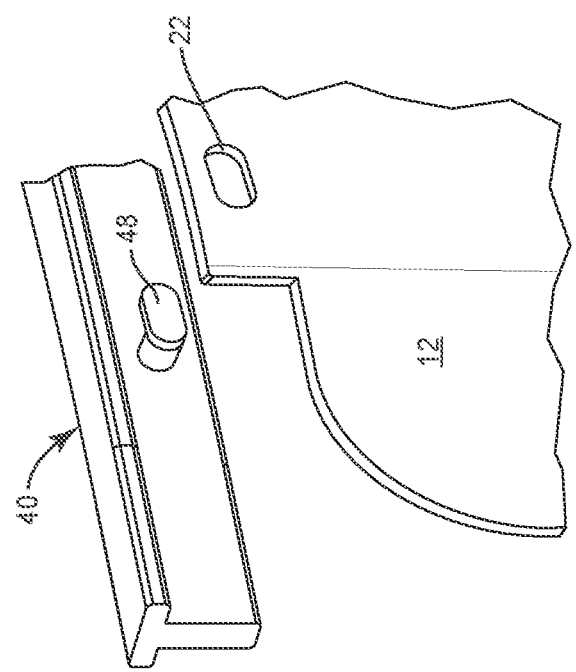
FIG. 11 illustrates a quick release mechanism for securing the transparent shield to the frame.

In some embodiments of the protective shield 10, a quick release mechanism is provided for attaching the transparent shield 12 to the frame 40. In one embodiment, shown in FIG. 11, the transparent shield 12 is provided with quick release slots 22 along the top edge 14. Rotatable clips 48 attached to the frame 40 can be inserted through the slots and turned to clamp the transparent shield 12 to the frame 40.

Figure 12:
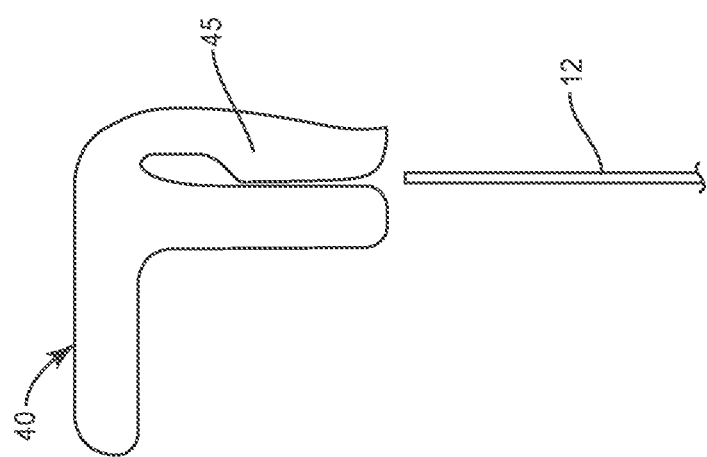
FIG. 12 illustrates clip for securing the transparent shield to the frame.

In another embodiment, shown in FIG. 12, the frame 40 comprises an angle with an integral clip and the top edge of the transparent shield 12 is inserted between the frame 40 and the integral clip 45 to mount the transparent shield 12. A single clip 45 can extend substantially the entire length of the frame 40, or multiple clips 45 can be provided at spaced locations along the frame 40.

Once the transparent shield 10 is mounted to the frame 40, a cover 60 can be attached to the front of the transparent shield 12 to cover the slot 32. The cover 60 includes a series of small pegs 62 that pass through corresponding openings 34 along the slot 32 and engage with openings 43 in the front plate 42 of the frame 40. The cover 60 blocks any splatter that may pass through the slot 32 in the transparent shield 12.

The protective shield 10 is designed to mount directly to the microscope 100 and to be self-supporting. Generally, the microscope 100 includes a main body 102 and an optical unit 104, sometimes referred to as binoculars. The optical unit 104 can attach directly to the main body 102 or may be connected to the main body 102 via an adapter 106. The protective shield 10 can be mounted to the main body 102, to the optical unit 104, or to an adapter 106. The protective shield 10 is mounted to provide the operator (e.g., surgeon) a comfortable distance from the shield 10 while preserving the ability to keep his/her eyes against the ocular.

In some embodiments, a seal or gasket 70 is provided around the periphery of the central opening 30. The seal or gasket 70 provides a tighter fit between the transparent shield 12 and the microscope 10. In some embodiments, the seal or gasket 70 comprises an elastomeric ring that engages the perimeter of the central opening 30 in the transparent shield 12. The elastomeric ring frictionally fits around the microscope 100 to help prevent rotation or tilting of the protective shield 12. Additionally, the elastomeric ring prevents fluids from seeping through any gap between the transparent shield 12 and the microscope 100. In some embodiments, the elastomeric ring enables the transparent shield 12 to fit microscopes 100 of slightly different dimensions and/or geometries. In other embodiments, the seal or gasket is over-molded on the transparent shield.

FIGS. 13A-13C illustrate a seal or gasket 70 according to one embodiment. In this embodiment, the seal or gasket comprise a strip 72 of elastomeric material that is bent to form an elastomeric ring with the ends of the strip 72 butting in end-to-end fashion. A connector 79 with two tabs 77 secures the ends of the strip 72 together to form the ring. The tabs 77 of the connector 79 insert into slots 74 in the ends of the strip 72.

FIGS. 14A-14C illustrate a seal or gasket 70 according to another embodiment. In this embodiment, the seal or gasket 70 comprise a strip 72 of elastomeric material that is bent to form a ring with the ends of the strip overlapping. The strip 72 includes opening 76 at each end that align when the ends are overlapped. The ends are secured by mating snap fasteners 78.

In both of the embodiments described above, the outer surface of the strip 72 can include a series of groves 75 that engage with the periphery of the central opening 30 in the transparent shield 12 and allows for some tilting and/or adjustment.

In an embodiment shown in FIGS. 15-18, a separate adapter 80 is provided for mounting the transparent shield 12 to a surgical microscope 100. Note that the adapter 80 is not the same as the adapter referred to earlier which is part of the microscope 100. The adapter 80 is designed to be installed between the main body 102 of the surgical microscope and the binoculars 104 as shown in FIG. 9 below. The adapter 80 may need to be specially configured for the particular instrument with which it is used.

Figure 15:
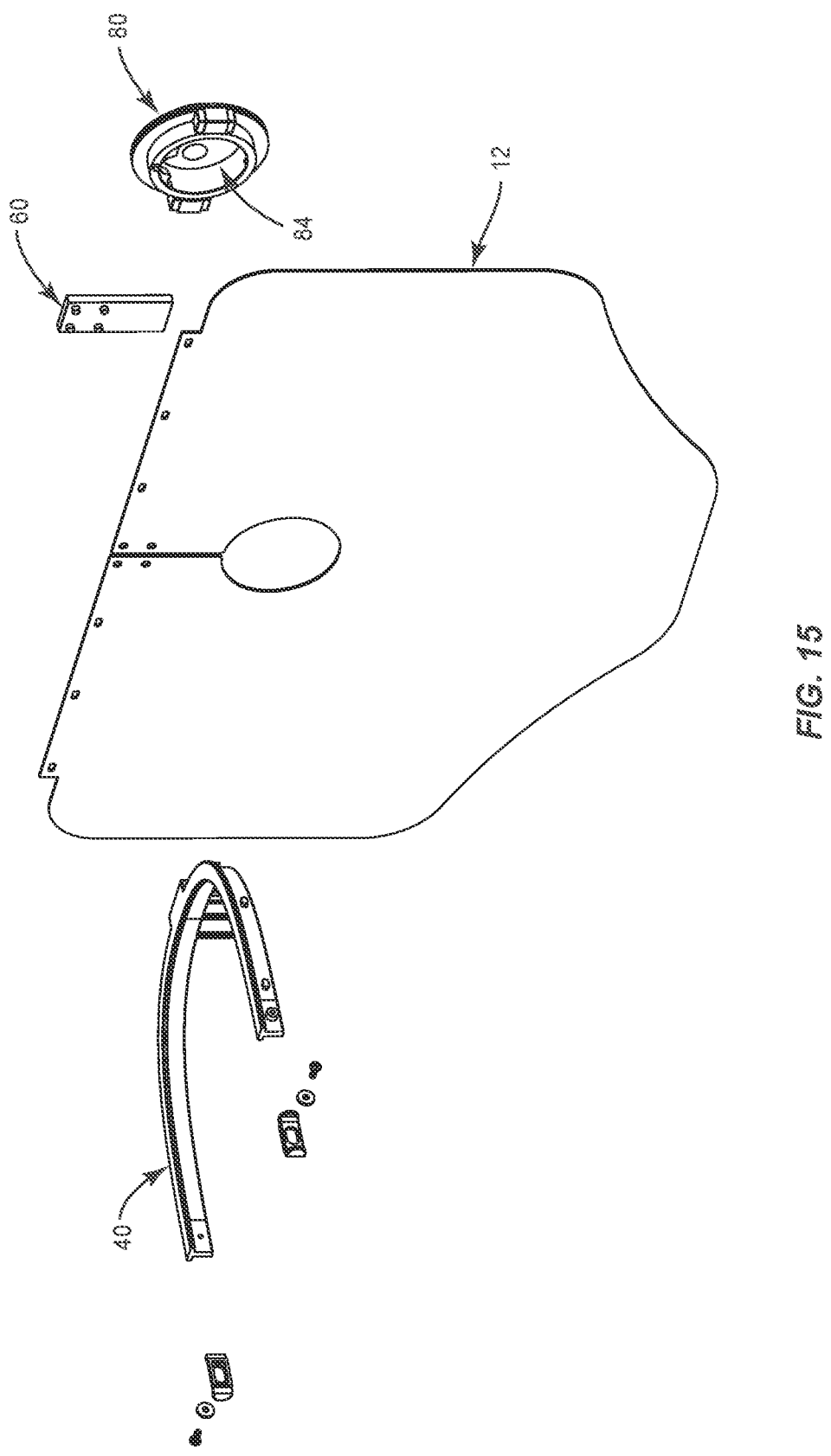
FIG. 15 is an exploded perspective view illustrating a surgical microscope and adapter for mounting the protective shield to the surgical microscope.
Figure 17:
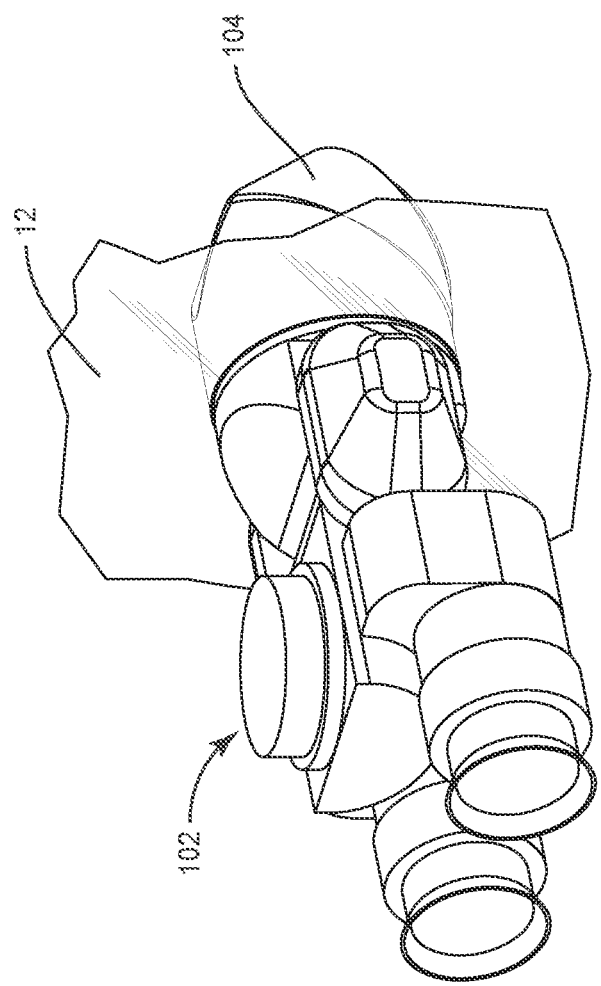
FIG. 17 is a perspective view illustrating the protective shield mounted to a surgical microscope using an adapter.
Figure 18:
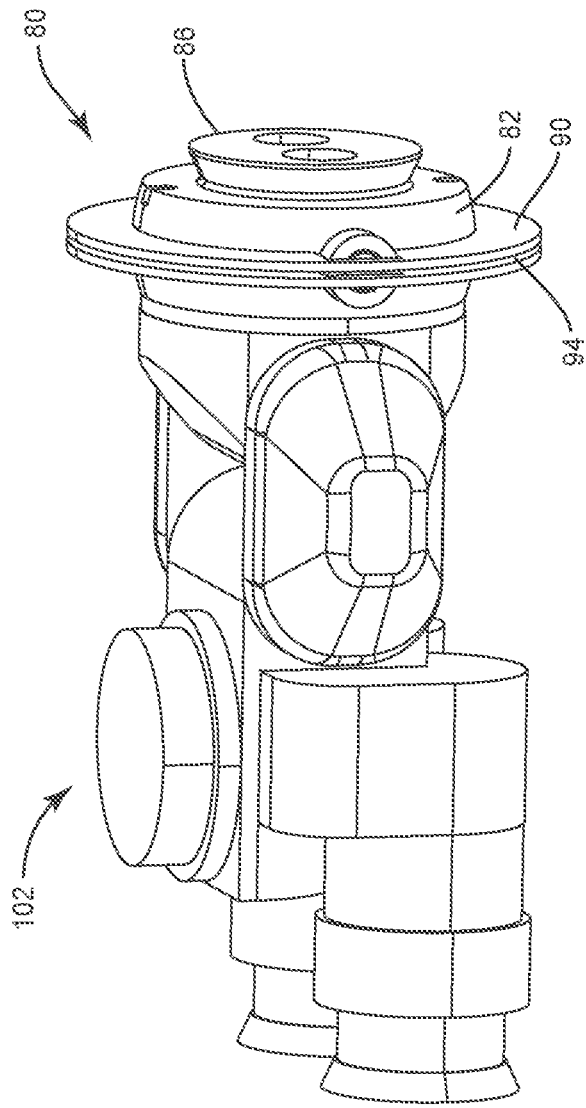
FIG. 18 is a perspective view of the adapter mounted to the binocular of a surgical microscope.

FIG. 15 is an exploded perspective view of a protective shield 10 with an adapter 80 as herein described. This embodiment is essentially the same as the previous embodiment with the seal of gasket 70 being replaced by the adapter 80 for mounting the protective shield 10 to the microscope 100. FIG. 16 is an exploded perspective view that showing the relation of the adapter 80 to the main body 102 and binocular 104. FIG. 17 shows the protective shield 10 assembled with the microscope 100. FIG. 18 shows the adapter 80 mounted to the binocular 104 of the microscope 100.

Figure 19:
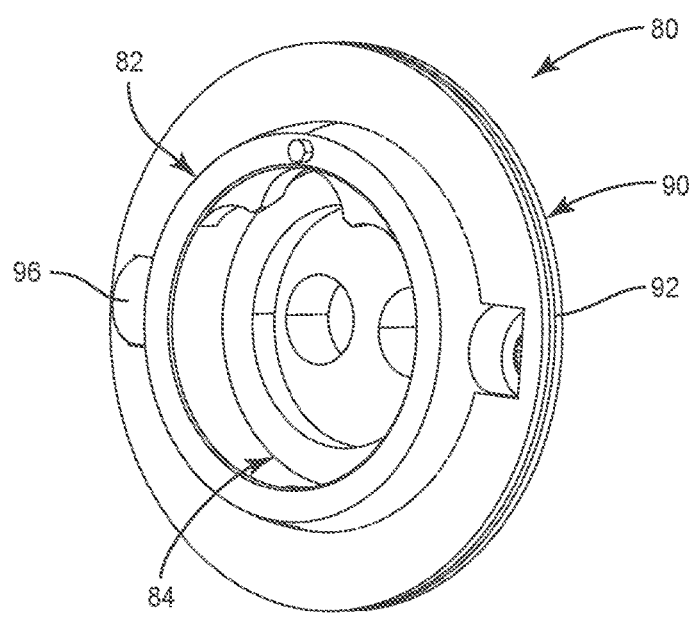
FIG. 19 is a perspective view of an adapter for mounting the protective shield to the surgical microscope.
Figure 20:
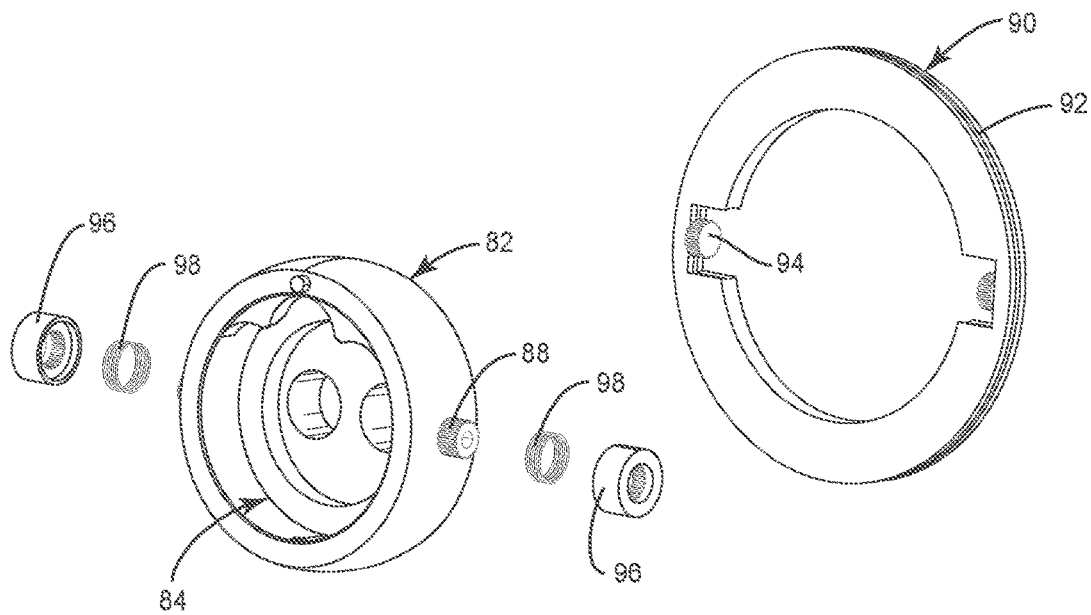
FIG. 20 is an exploded perspective view of an adapter for mounting the protective shield to the surgical microscope.
Figure 21:
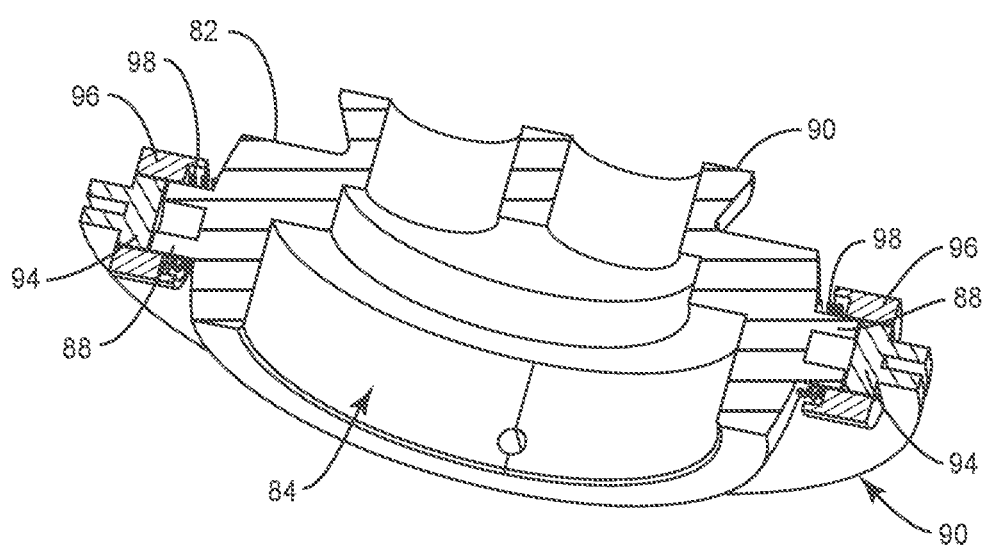
FIG. 21 is a section view of the adapter.

The design of the adapter 80 is shown in more detail in FIGS. 19-20. Generally, the adapter 80 includes a generally cylindrical adapter body 82 having a receptacle 82 on one side configured to receive the binocular 102 of the microscope 100 and a dovetail-shaped extension 86, shown in FIG. 18, on the opposite side configured to mate with the main body 102 of the microscope 100. A seal 90 surrounds the adapter body 82 and includes a groove 92 in the outer periphery thereof to receive the edge of the transparent shield 12 surrounding the central opening 30. The seal 90 is mounted to the adapter body 82 by a tilt mechanism that allows the protective shield 10 to rotate forward and backward relative to the adapter body 82 after it is installed on the surgical microscope 100.

FIG. 20 is an exploded perspective view showing the tilt mechanism in more detail. The adapter body 82 includes diametrically opposed shafts 88 with splines on the outer surface thereof. The splines extend parallel to the axis of the shafts 88. The seal 90 likewise includes inwardly projecting mounting shafts 94 with splines on the outer surface thereof. Release buttons 96 are mounted on the shafts 88, 94 and are movable in the axial direction between locked and unlocked positions. The inner bores of the release buttons 96 include splines that engage with the splines on the shafts 88, 94 for both the adapter body 82 and the seal 90. Springs 98 bias the release buttons 96 to the locked position. In the locked position, the, the splines on the release buttons engage with the splines on the shafts 88, 94 for both the adapter body 82 and the seal 90. The release buttons 96 can be pressed inward against the force of the springs 98 to an unlocked position. In the unlocked position, the splines on the release buttons 96 remain engaged with the splines on the shafts 88 for the adapter body 82 and disengage from the splines on the shafts 94 for the seal 90. This disengages the seal 90 and allows it to rotate/tilt about the axis of the shafts 88, 94. This allows adjustment of the tilt angle in the fore-aft direction of the protective shield 10.

The embodiments described to this point all include a frame 40 to retain the transparent shield 12 in a curved configuration. In an alternate embodiment, referred to herein as the frameless design, a frameless shield 12 is made of a transparent sheet material, such as acrylic or polycarbonate, that can be formed into and hold a desired shape without the need for a frame 40. FIG. 8B illustrates a frameless shield 12 before being formed into a curved shape. The frameless shield 12 includes a center opening 30 and slot 32 as previously described and is curved into the desired form but holds its shape without the frame 40. The center opening 30 is configured to mount the frameless shield 12 on the outer surface of the surgical microscope 100 as previously described and may include a seal or gasket.

What is claimed is:

1. A protective shield for a surgical microscope, the protective shield comprising:
   a flexible shield made of a transparent sheet material, the flexible shield including a central opening that fits around the surgical microscope;
   a frame bent to form an arc curving concavely towards the user when the protective shield is mounted to the surgical microscope;
   wherein the frame is configured to removably attach to an upper edge of the flexible shield to hold the flexible shield in a curved configuration forming a concave arc around the user; and a plurality of fasteners spaced along the frame configured to removably secure the flexible shield to the frame; wherein the fasteners comprise at least one slide member mounted adjacent an end of the frame, the slide member being configured to slide between an unlocked position to enable the flexible shield to be installed or removed and a locked position in which the slide member extends over the edge of the flexible shield to secure the flexible shield to the frame.

2. The protective shield of claim 1, wherein the plurality of fasteners comprise two slide fasteners adjacent respective opposing ends of the frame.

3. The protective shield of claim 2, further comprising:
a plurality of openings spaced along an upper edge of the flexible shield; and
a plurality of studs connected to the frame for engagement with respective openings in the flexible shield for aligning and locating the flexible shield with respect to the frame.

4. The protective shield of claim 3, wherein the frame includes a center support at an approximate midpoint of the frame, the center support including a slot to receive the upper edge of the flexible shield when the flexible shield is attached to the frame.

5. The protective shield of claim 1, wherein the flexible shield further comprises a slot extending from the central opening to an edge of the shield.

6. The protective shield of claim 5, further comprising a cover extending over the slot in the flexible shield.

7. The protective shield of claim 1, further comprising an elastomeric seal surrounding the central opening configured to frictionally engage an outer surface of the surgical microscope.

8. The protective shield of claim 1, further comprising an adapter insertable into the central opening for mounting the flexible shield to the surgical microscope.

9. The protective shield of claim 8, wherein the adapter includes a tilt mechanism for adjusting a tilt angle of the flexible shield.

10. A protective shield for a surgical microscope, the protective shield comprising:
a flexible shield made of a transparent sheet material, the flexible shield including a central opening that fits around the surgical microscope;
a frame bent to form an arc curving concavely towards the user when the protective shield is mounted to the surgical microscope;
wherein the frame is configured to removably attach to an upper edge of the flexible shield to hold the flexible shield in a curved configuration forming a concave arc around the user;
a plurality of fasteners spaced along the frame configured to removably secure the flexible shield to the frame; wherein:
the flexible shield includes a plurality of slots spaced along an upper edge of the flexible shield;
the plurality of fasteners comprise a plurality of rotating clips spaced along the frame for insertion through respective slots in the flexible shield; the rotatable clips being movable from a first position enabling the rotating clip to pass through a respective slot in the flexible shield and a second position extending over the flexible shield to removably secure the flexible shield to the frame.

11. The protective shield of claim 10, wherein the frame includes a center support at an approximate midpoint of the frame, the center support including a slot to receive the upper edge of the flexible shield when the flexible shield is attached to the frame.

12. The protective shield of claim 10, wherein the flexible shield further comprises a slot extending from the central opening to an edge of the shield.

13. The protective shield of claim 12, further comprising a cover extending over the slot in the flexible shield.

14. The protective shield of claim 10, further comprising an elastomeric seal surrounding the central opening configured to frictionally engage an outer surface of the surgical microscope.

15. The protective shield of claim 10, further comprising an adapter insertable into the central opening for mounting the flexible shield to the surgical microscope.

16. The protective shield of claim 15, wherein the adapter includes a tilt mechanism for adjusting a tilt angle of the flexible shield.

17. A surgical instrument comprising:
a surgical microscope; and
a protective shield removably mounted to the surgical microscope, the protective shield comprising:
a flexible shield made of a transparent sheet material, the flexible shield including a central opening that fits around the surgical microscope;
a frame bent to form an arc curving concavely towards the user when the protective shield is mounted to the surgical microscope;
wherein the frame is configured to removably attach to an upper edge of the flexible shield to hold the flexible shield in a curved configuration forming a concave arc around the user;
a plurality of fasteners spaced along the frame configured to removably secure the flexible shield to the frame; wherein the fasteners comprise at least one slide member mounted adjacent an end of the frame, the slide member being configured to slide between an unlocked position to enable the flexible shield to be installed or removed and a locked position in which the slide member extends over the edge of the flexible shield to secure the flexible shield to the frame.

18. The surgical instrument of claim 17, wherein the flexible shield further comprises a slot extending from the central opening to an edge of the shield.

19. The surgical instrument of claim 18, further comprising a cover extending over the slot in the flexible shield.

20. The surgical instrument of claim 17, further comprising an elastomeric seal surrounding the central opening configured to frictionally engage an outer surface of the surgical microscope.

21. The surgical instrument of claim 17, further comprising an adapter insertable into the central opening for mounting the flexible shield to the surgical microscope.

22. The surgical instrument of claim 21, wherein the adapter includes a tilt mechanism for adjusting a tilt angle of the flexible shield.

* * * * *